US00PP24197P2

(12) United States Plant Patent
Kordes

(10) Patent No.: US PP24,197 P2
(45) Date of Patent: Jan. 28, 2014

(54) MINIATURE ROSE PLANT NAMED 'KORSCAMER'

(50) Latin Name: *Rosa hybrida*
Varietal Denomination: KORscamer

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 86 days.

(21) Appl. No.: 13/385,830

(22) Filed: Mar. 7, 2012

(51) Int. Cl.
*A01H 5/00* (2006.01)

(52) U.S. Cl.
USPC ..... Plt./122; Plt./101; Plt./116

(58) Field of Classification Search
USPC ..... Plt./101, 116, 122
See application file for complete search history.

*Primary Examiner* — Susan McCormick Ewoldt

(57) ABSTRACT

A new and distinct variety of rose with long lasting, novel red flowers, and attractive foliage with average disease resistance. It exhibits moderate to vigorous growth and an upright habit with abundant flowers. The new variety propagates well from cuttings. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The present discovery constitutes a new and distinct variety of a miniature pot rose plant which was discovered in a cultivated area in the inventor's nursery in Offenseth-Sparrieshoop, Germany. The new rose variety resulted from a naturally occurring mutation of unknown causation on a branch of 'KORsavale', an unpatented miniature rose variety.

The new rose plant was asexually propagated for further evaluation. This new and distinctive miniature rose variety is named 'KORscamer'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from 'KORsavale' by the following combination of characteristics:

1. 'KORscamer' has velvet red flowers, whereas 'KORsavale' has orange red flowers.
2. 'KORscamer' has reddish juvenile shoots, whereas 'KORsavale' has green juvenile shoots.

This mutation was selected to develop a new rose variety with:

1. Uniform growth and flowering;
2. Abundant attractive, large, long lasting red flowers; and
3. Attractive and abundant foliage.

This combination of qualities is not present in prior rose cultivars known to the inventor. These objectives have been substantially achieved and in that distinguish 'KORscamer' from all other varieties of which I am aware.

As part of a rose development program, Tim-Hermann Kordes conducted evaluations and observations on the mutation in a controlled environment in Offenseth-Sparrieshoop, Germany. 'KORscamer' exhibited distinctive physical and biological characteristics. The new rose plant 'KORscamer' was selected in June, 2007, from a population of the parent varieties and asexually propagated for further evaluation. The first asexual propagation of 'KORscamer' was done by rooting cuttings in July, 2007 at the inventor's nursery in Offenseth-Sparrieshoop, Germany.

This initial and other subsequent propagations conducted in controlled environments demonstrate that 'KORscamer' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORscamer'.

DETAILED BOTANICAL DESCRIPTION

The following is a description of 'KORscamer', as observed growing in a nursery in Jackson County, Oreg., in October 2011, on plants of 5 months of age. Color references are made using The Royal Horticultural Society (London, England) Colour Chart, 2001 except where common terms of color are used.

For a comparison, several physical characteristics of the rose variety 'KORpusiro', a rose variety from the same inventor described and illustrated in U.S. Plant Pat. No. 12,601 and issued on May 7, 2002, are compared to 'KORscamer' in Chart 1.

CHART 1

| Characteristic | 'KORscamer' | 'KORpusiro' |
|---|---|---|
| But color at first opening | Red-Purple Group 59A | Red Group 53D |
| Petal count | Approximately 27 | 35 to 40 |
| Number of pistils | 40 to 50 | 60 to 80 |

Parent: 'KORsavale'.
Classification:
*Botanical classification.*—*Rosa hybrida* 'KORscamer'.
*Commercial classification.*—Miniature rose.

FLOWER AND FLOWER BUD

Blooming habit: Continuous.
Flower bud:
*Size.*—Upon opening, 20 to 25 mm in length from base of receptacle to distal end of bud and 12 to 16 mm diameter at its widest point.
*Bud form.*—Globular with a high center.
*Bud color.*—As sepals first unfold, bud color is Red-Purple Group 59A. When ¼ open, the upper surface of petals is dark vibrant red. Red Group 53A on the upper side of outer petals, some with Yellow Group 146A and Green-White Group W157A. The lower surface is Red-Purple Group 59A with intonations of Yellow Group 146A and Greyed-Purple Group 187A.
*Sepals.*—Color: Upper surface Green Group 146A. Lower surface is Green Group 147A. Size: Average 20 to 22 mm long and 7 to 9 mm wide. Shape: Weak foliaceous appendages on three of the five sepals. Apex: Apiculate and somewhat cirrose. Base: Flat at union with receptacle. Quantity: Five. Surface texture: Limited pubescence with fine hairs on upper and lower surfaces and margins. Margins: Entire.
Receptacle:
*Surface.*—Smooth with fine white hairs and very few stipitate glands.
*Color.*—Yellow-Green Group 146A.
*Shape.*—Urn-shaped to broad funnel shaped.
*Size.*—5 mm high and 10 mm wide.
Peduncle:
*Surface.*—With a few fine hairs and a few stipitate glands.
*Length.*—35 to 45 mm average length.
*Diameter.*—1 to 1.5 mm average diameter.
*Color.*—Green Group 137A.
*Strength.*—Strong.
*Borne.*—Singly.
Flower bloom:
*Fragrance.*—None.
*Duration.*—Long lasting, on the plant 10 to 12 days. Senesced petals drop away cleanly.
*Size.*—Large for a miniature rose. When open, the average flower diameter is 55 mm and the average flower height is 25 mm.
*Form.*—Shape of flower when viewed from the side: Upon opening, upper part: Flattened convex. Upon opening, lower part: Convex. Open flower, upper part: Flattened convex. Open flower, lower part: Flattened convex.
Color:
*Upon opening, petals.*—Outermost petals: Outer Side: Red-Purple Group 59A. Inner Side: Red Group 53A. Innermost petals: Outer Side: Red-Purple Group 59A. Inner Side: Red Group 53A.
*Upon opening, basal petal spots.*—Basal petal spot, outermost petals: Outer Side: Green-White Group 157D. Inner Side: Green-White Group 157A. Basal petal spot, innermost petals: Outer Side: Green-White Group 157D. Inner Side: Green-Yellow Group 1D.
*After opening, petals.*—Outermost petals: Outer Side: Red-Purple Group 59A. Inner Side: Red Group 53A. Innermost petals: Outer Side: Red-Purple Group 59A. Inner Side: Red Group 53A.
*After opening, basal petal spots.*—Basal petal spot, outermost petals: Outer Side: Green-White Group 157D. Inner Side: Green-White Group 157A. Basal petal spot, innermost petals: Outer Side: Green-White Group 157D. Inner Side: Green-Yellow Group 1D.
General tonality: On open flower Red Group 53A. No change in the general tonality at the end of the 5$^{th}$ day. Afterwards, general tonality is Red Group 53B.
Petals:
*Petal count.*—Double. Average Range: Approximately 27 petals under normal conditions.
*Petal reflex.*—Petals reflex slightly.
*Petal edge.*—Entire.
*Petal shape.*—Round. Apex shape is round. Shape of base is rounded.
*Petal size.*—24 to 26 mm long and 28 to mm wide.
*Thickness.*—Average.
*Petal arrangement.*—Not formal.
Petaloids:
*Petaloid count.*—Average of 2 to 3 per flower.
*Petaloid size.*—Petaloids are 12 mm long and 10 mm wide.
*Petaloid color.*—Color of inner side is Red Group 53A. Color of outer side is Red-Purple Group 59A.
*Petaloid texture.*—Surface of inner side is velvet like.
*Margins.*—Smooth, entire.
*Petaloid shape.*—Rounded. Apex: Ovate. Base: Rounded to ovate.
Reproductive organs:
*Pistils.*—Approximately 40 to 50 present. Stigmas: Location: Slightly superior in position to anthers. Color: Green-White Group 157A and Green-Yellow Group 160D with intonations of Red-Purple Group 59A above. Styles: Length: About 5 mm long. Color: Green-White Group 157A.
*Stamens.*—Approximately 40 to 45 on average and regularly arranged. Anthers: Size: Average 5 to 7 mm long. Pollen: Not observed. Color: Greyed-Orange Group 163A. Filaments: Color: Red-Purple Group 59A. Length: About 4 to 5 mm.

THE PLANT

*Growth.*—Moderate to vigorous growth.
*Plant habit.*—Upright habit. When grown as a 15 cm container plant, the average plant height is 25 to 30 cm and the average plant width is 20 cm.
*Stems.*—Stem color: Juvenile wood: Green Group 137A. Mature wood: Green Group 137A. Stem surface: Juvenile wood: Smooth. Mature wood: Smooth.
*Prickles.*—Present. Incidence: Average of 14 to 16 per each 10 cm of stem. Size: Average length: 3 to 4 mm. Color: Immature prickles: Orange-White Group 159C at base. Otherwise Green-White Group 157A. Mature prickles: Greyed-Orange Group 164C. Senescing to Greyed-Orange Group 164D. Shape: Linear. Anthocyanin: Present on juvenile thorns, color of Greyed-Purple Group 183C.
*Leaves and leaflets.*—Normally 5 leaflets on normal leaves in middle of the stem. Venation pattern: Pyramidal net pattern. Leaf size: 80 to 85 mm long and 60 to 70 mm wide. Abundance: Average. Texture: Somewhat leathery. Upper side of leaflet: Semi-glossy and smooth. Under side of leaflet: Matte and rough.

*Color, mature foliage*.—Upper Leaf Surface: Green Group 137A. Lower Leaf Surface: Green Group 138A.

*Color, juvenile foliage*.—Upper Leaf Surface: Green Group 137A with intonations of Greyed-Purple Group 183D. Lower Leaf Surface: Greyed-Purple Group 183D. Anthocyanin intonation: Intonations of Greyed-Purple Group 183D present on upper and lower leaflets.

*Stipules*.—Size: 8 to 12 mm long, 6 to 8 mm from distal tip to distal tip and 5 mm wide on body. Stipule color: Green Group 138A. Anthocyanin: Greyed-Purple Group 183D. Stipitate glands: Present. Margins: Serrated. Shape: Apex: Pointed. Base: Flat.

*Petiole*.—Length: Length varies between 5 to 15 mm. Diameter: Average 1.0 mm. Petiole color: Green Group 137A. Underneath: Smooth with limited numbers of stipitate glands. Margins: None to a few hairs with stipitate glands and prickles. Anthocyanin: Red-Purple Group 183D. Prickles: A few underneath. Stipitate Glands: Few to none.

*Petiole rachis*.—Length: Average 10 to 15 mm. Diameter: Average 1.0 mm. Color: Green Group 137A. Margins: None to a few hairs with stipitate glands and prickles. Anthocyanin: Red-Purple Group 183D. Prickles: A few underneath. Stipitate Glands: Few to none.

*Leaflets*.—Size: Average size of the terminal leaflet is 40 to 50 mm long and 25 to 30 mm wide. Shape: Ovate. Base: Obtuse. Apex: Acute. Margins: Finely serrated. Surface: Upper: Semi-glossy. Lower: Matte. Texture: Smooth. Arrangement: Odd pinnate Venation: Reticulate.

Hips/seed formation: None observed.

Winter hardiness: To date, the variety has been grown successfully in USDA Zones 5 to 9.

Disease resistance: Good resistance to Botrytis (*Botrytis cinerea*) disease under normal growing conditions.

I claim:

1. A new and distinct variety of rose plant, as described and illustrated herein.

* * * * *

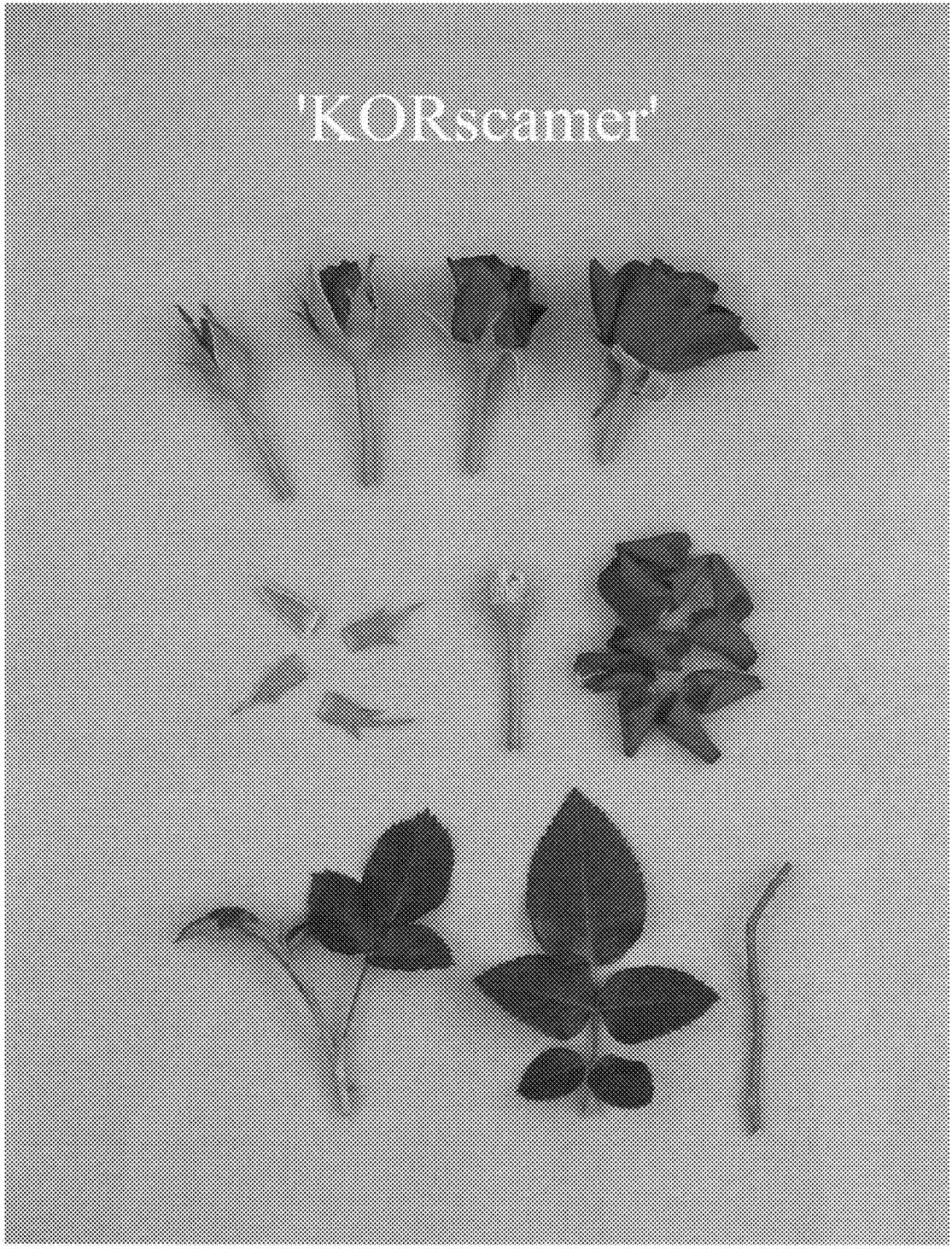
'KORscamer'